US009627188B2

(12) United States Patent
Ariya et al.

(10) Patent No.: US 9,627,188 B2
(45) Date of Patent: Apr. 18, 2017

(54) METHOD AND SYSTEM FOR THE QUANTITATIVE CHEMICAL SPECIATION OF HEAVY METALS AND OTHER TOXIC POLLUTANTS

(71) Applicants: Parisa A. Ariya, Hampstead (CA); Farhad Raofie, Tehran (IR); Daniel Deeds, Montreal (CA)

(72) Inventors: Parisa A. Ariya, Hampstead (CA); Farhad Raofie, Tehran (IR); Daniel Deeds, Montreal (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 14/549,041

(22) Filed: Nov. 20, 2014

(65) Prior Publication Data

US 2015/0206726 A1 Jul. 23, 2015

Related U.S. Application Data

(63) Continuation of application No. 13/391,093, filed as application No. PCT/CA2010/001274 on Aug. 18, 2010, now abandoned.

(Continued)

(51) Int. Cl.
*H01J 49/04* (2006.01)
*H01J 49/00* (2006.01)
(Continued)

(52) U.S. Cl.
CPC .......... *H01J 49/0022* (2013.01); *G01N 1/405* (2013.01); *G01N 15/06* (2013.01);
(Continued)

(58) Field of Classification Search
CPC .. G01N 1/405; G01N 33/1813; G01N 30/728; G01N 15/06; H01J 49/04;
(Continued)

(56) References Cited

U.S. PATENT DOCUMENTS 3,768,302 A * 10/1973 Barringer ........... G01N 33/0011
436/178
3,970,428 A * 7/1976 Barringer ............... G01V 9/007
422/83

(Continued)

FOREIGN PATENT DOCUMENTS

CA 2011295 9/1990
CA 2559847 10/2005

(Continued)

OTHER PUBLICATIONS

Poulain, Alexandre J., et al., Redox transformations of mercury in an Arctic snowpack at springtime, AE International—Polar Regions, Atmospheric Environment 38 (2004) 6763-6774, December.

(Continued)

*Primary Examiner* — Wyatt Stoffa
(74) *Attorney, Agent, or Firm* — Leason Ellis LLP

(57) ABSTRACT

This invention relates to systems and methods for measuring quantitatively multiple species or heavy metals, including mercury, and other toxic pollutants. More specifically, the systems and methods of the invention allows for determination of the analytes even at very low concentration, through concentration on a collection interface, desorption and analysis by mass spectrometry. The invention also provides for a portable device or kit for modifying an existing mass spectrometer.

10 Claims, 17 Drawing Sheets

Related U.S. Application Data

(60) Provisional application No. 61/235,034, filed on Aug. 19, 2009.

(51) Int. Cl.
  *G01N 1/40* (2006.01)
  *G01N 33/18* (2006.01)
  *G01N 15/06* (2006.01)
  *H01J 49/26* (2006.01)

(52) U.S. Cl.
  CPC .......... *G01N 33/1813* (2013.01); *H01J 49/04* (2013.01); *H01J 49/26* (2013.01)

(58) Field of Classification Search
  CPC .. H01J 49/0404; H01J 49/145; H01J 49/0022; H01J 49/26
  See application file for complete search history.

(56) References Cited

U.S. PATENT DOCUMENTS

| | | | | |
|---|---|---|---|---|
| 4,137,751 A * | 2/1979 | Rhodes | G01V 5/025 | 73/28.04 |
| 4,374,090 A * | 2/1983 | McClure | G01N 27/70 | 250/432 R |
| 4,573,354 A * | 3/1986 | Voorhees | G01V 9/007 | 436/25 |
| 5,140,845 A * | 8/1992 | Robbins | G01N 1/2226 | 73/19.03 |
| 5,425,263 A * | 6/1995 | Davies | G01N 1/2214 | 73/28.05 |
| 5,511,409 A * | 4/1996 | Knaebel | B01D 53/0454 | 73/28.01 |
| 5,561,066 A | 10/1996 | Sinha | | |
| 6,852,970 B2 * | 2/2005 | Yamada | H01M 8/04082 | 250/281 |
| 7,062,982 B2 * | 6/2006 | Coyle | B01D 50/004 | 73/863.23 |
| 7,208,030 B2 * | 4/2007 | Totoki | B03C 3/017 | 95/3 |
| 7,335,897 B2 | 2/2008 | Takats et al. | | |
| 7,847,244 B2 | 12/2010 | Venter et al. | | |
| 8,071,957 B1 * | 12/2011 | Ludwig | H01J 49/168 | 250/282 |
| 8,203,117 B2 | 6/2012 | Wiseman et al. | | |
| 8,277,767 B2 * | 10/2012 | Ariya-Far | B01D 53/82 | 210/600 |
| 8,410,452 B2 | 4/2013 | Koenig et al. | | |
| 2003/0000318 A1 * | 1/2003 | Schroeder | G01N 1/2205 | 73/863.23 |
| 2004/0104342 A1 * | 6/2004 | Yamada | H01M 8/04082 | 250/288 |
| 2007/0164209 A1 * | 7/2007 | Balogh | H01J 49/145 | 250/288 |
| 2008/0028930 A1 * | 2/2008 | Danilchik | G01N 1/28 | 95/87 |
| 2008/0302237 A1 * | 12/2008 | Grate | G01N 1/2214 | 95/18 |
| 2009/0260421 A1 * | 10/2009 | Danilchik | G01N 1/28 | 73/23.41 |
| 2010/0011663 A1 * | 1/2010 | Coyle | F25J 1/0022 | 48/127.3 |
| 2010/0078550 A1 | 4/2010 | Wiseman et al. | | |
| 2010/0116021 A1 * | 5/2010 | O'Brien | G01N 1/2202 | 73/23.37 |
| 2010/0253933 A1 * | 10/2010 | Guieze | G01N 21/33 | 356/51 |
| 2011/0127421 A1 | 6/2011 | Finlay | | |
| 2011/0158872 A1 * | 6/2011 | Ariya | B01D 53/82 | 423/219 |
| 2011/0299072 A1 * | 12/2011 | Yamada | G01N 33/2835 | 356/319 |
| 2012/0184039 A1 * | 7/2012 | Alper | G01N 1/2035 | 436/76 |
| 2012/0205533 A1 * | 8/2012 | Ariya | G01N 1/405 | 250/282 |
| 2012/0312979 A1 | 12/2012 | Cooks et al. | | |
| 2013/0040393 A1 | 2/2013 | Jiao et al. | | |
| 2013/0292564 A1 | 11/2013 | Ouyang et al. | | |
| 2014/0007710 A1 * | 1/2014 | Danilchik | G01N 1/28 | 73/863.21 |
| 2014/0051180 A1 | 2/2014 | Cooks et al. | | |

FOREIGN PATENT DOCUMENTS

| | | |
|---|---|---|
| CA | 2671859 | 9/2008 |
| WO | WO 2005/104179 | 11/2005 |

OTHER PUBLICATIONS

Lalonde, Janick D., et al., "Photoinduced Oxidation of $HG^0$(aq) in the Waters from the St. Lawrence Estuary" Environ. Sci. Technol. 2004, 38, 508-514, December.

Raotie, Farhad et al., "Product Study of the Gas-Phase Br0-Initiated Oxidation of $Hg^0$: Evidence for Stable $Hg^{1+}$ Compounds" Environ. Sci. Technol. 2004, 38, 4319-4326, December.

Biswajit, Pal et al., "Gas-Phase H0*-Initiated Reactions of Elemental Mercury: Kinetics, Product Studies, and Atmospheric Implications" Environ. Sci. Technol. 2004, 38, 5555-5566, December.

Biswajit, Pal et al., "Studies of Ozone initiated reactions of gaseous mercury: kinetics, product studies, and atmospheric implications" Phys. Chem. Chem. Phys., 2004, 6, 572-579, December.

Ariya, Parisa et al., "The Arctic: a sink for mercury" Tellus 56B (2004), 5, pp. 397-404, December.

Engle, Mark A. et al., "The influence of ozone on atmospheric emissions of gaseous elemental mercury and reactive gaseous mercury from substrates" Atmospheric Environment, 39 (2005) 7506-7517, December.

Garcia, Edenise et al., "Diel variations in photoinduced oxidation of $Hg^0$ in freshwater" Chemosphere 59 (2005) 977-981, December.

Amyot, Marc et al., "Dark Oxidation of Dissolved and Liquid Elemental Mercury in Aquatic Environments" Environ. Sci. Technol. 2005, 39, 110-114, December.

Garcia, Edenise et al., "Relationship between DOC photochemistry and mercury redox transformations in temperate lakes and wetlands" Geochimica et Cosmochimica Acta, vol. 69, No. 8, pp. 1917-1924, 2005, December.

Poulain, Alexandre J. et al., "Potential for Mercury Reduction by Microbes in the High Arctic" Applied and Environmental Microbiology, Apr. 2007, p. 2230-2238.

Poulain, Alexandre J. et al., "Biological and Chemical Redox Transformations of Mercury in Fresh and Salt Waters of the High Arctic during Spring and Summer" Environ. Sci. Technol. 2007, 41, 1883-1888, December.

Poulain, Alexandre J. et al., "Mercury distribution, partitioning and speciation in coastal vs. inland High Arctic snow" Geochimica er Cosmochimica Acta, 71 (2007) 3419-3431, December.

Snider, Graydon et al., "Photo-catalytic oxidation reaction of gaseous mercury over titanium dioxide nanoparticle surfaces" Chemical Physics Letters 491 (2010) 23-28, December.

Ariya, Parisa A., "Mid-latitude mercury loss" Macmillan Publishers Limited 2011, vol. 4, Jan. 2011, pp. 14-15.

Vitolo, Sandra et al., "Deposition of sulfer from $H_2S$ on porous adsorbants and the effect on their mercury adsorption capacity" Geothermics 28 (1999) 341-354, December.

Alexander et al., "Quantitative Analysis of the Detection Limits for Heavy-Metal-Contaminated Soils by Laser-Induced Breakdown Spectroscopy", Department of Electrical Engineering/Center for Electro-Optics, University of Nebraska—Lincoln, NE, Jul. 31, 1996, pp. 1-30.

Zou et al., "An Environmental Automatic Monitoring System for Heavy Metals", IEEE International Conference on Control and Automation, China, 2007, pp. 798-801, NLT December.

(56) References Cited

OTHER PUBLICATIONS

Hall et al., "Development of a Mercury Vapour Air Analyser for Measurement of Hg in Solution", Water, Air, and Soil Pollution, vol. 111, 1999, pp. 287-295, NLT December.

Selid et al., "Sensing Mercury for Biomedical and Environmental Monitoring", Sensors, Jul. 2009, vol. 9, pp. 5446-5459.

Antipov et al., "Mercmy Environment Monitoring", Proc. SPIE, vol. 2504, vol. 448, 1995. pp. 448-452, NLT December.

Steffen A. et al., "A synthesis of atmospheric mercury depletion event chemistry in the atmosphere and snow" Atmos. Chem. Phys. 8, 1445-1482, Mar. 12, 2008.

Raofie, Farhad et al., "Reaction of gaseous mercury with molecular iodine, atomic iodine, and iodine oxide radicals—Kinetics, product studies, and atmospheric implications" Can. J. Chem. 86: 811-820, Published on Jul. 5, 2008.

Dastoor, Ashu et al., "Modeling Dynamic Exchange of Gaseous Elemental Mercury at Polar Sunrise" Environ. Sci. Technol. Apr. 8, 2008, 42, 5183-5188.

Si, Lin et al., "Reduction of Oxidized Mercury Species by Dicarboxylic Acids ($C_2$-$C_4$): Kinetic and Product Studies" Environ. Sci. Technol. Apr. 10, 2008, 42, 5150-5155.

Snider, Graydon et al., "Effects of relative humidity and CO(g) on the $O_3$-initiated oxidation reaction of $Hg^0(g)$: kinetic & product studies" Phys. Chem. Chem. Phys., Published on Jul. 24, 2008, 10, 5616-5618.

Ariya, Parisa A. et al., "Chemical Transformation of Gaseous Elemental Mercury in the Atmosphere" Departments of Chemistry and Atmospheric and Oceanic Sciences, McGill University, Chapter 12—Chemical Transformation of GEM, pp. 261-294, Jul. 22, 2005.

Ariya, Parisa A. et al., "Mercury Chemical Transformation in the Gas, Aqueous and Heterogeneous Phases: State-of-the-art Science and Uncertainties" Mercury Fate and Transport in the Global Atmosphere, Springer Sciences + Business Media, LLC, DOI: 10.1007/979-0-387-93958-2_15, Chapter 15—Major Chemical and Physical Processes of Mercury Dynamics, Mar. 3, 2009, pp. 459-501.

Deeds, Daniel; Ghoshdastidar, Avik; Raofie, Farhad; Guerette, Elise-Andre; Tessier, Alain; Ariya, Parisa, "Development of a Particle-Trap Preconcentration-Soft Ionization Mass Spectrometric Technique for the Quantification of mercury halides in air", Analytical Chemistry, DOI: 10.1021/ac504545w, Apr. 2, 2015, pp. 5109-5116.

Ariya, Parisa A.; Amyot, Marc; Dastoor, Ashu; Deeds, Daniel; Subir, Mahamud; Feinberg, Aryeh; Kos, Gregor; Poulain, Alexandre; Ryjkov, A; Semeniuk, Kirill; Toyota, Kenjiro, "Mercury Physicochemical and Biogeochemical Transformation in the Atmosphere and at Atmospheric Interfaces: A Review and Future Directions", Chemical Reviews (American Chemical Society), DOI: 10.1021/cr500667e, Apr. 30, 2015. pp. A-AQ.

P. A. Ariya, A. F. Khalizov, and A. Gidas, "Reaction of Gaseous Mercury with Atomic and Molecular Halogens: Kinetics, Product Studies, and Atmospheric Implications", Journal of Physical Chemistry A, 106(32), 7310-7320, May 24, 2002. pp. 7310-7320.

P.A. Ariya, A P. Dastoor, M. Amyot, W.H. Schroeder, L. Barrie, K. Anlauf, F. Raofie, A. Ryzkhov, D. Davignon; J. Lalonde, A. Steffen, "The Arctic: A sink for mercury", Tellus B, 56, 5, 397-403, Apr. 13, 2004, pp. 397-403.

F. Raofie and P.A. Ariya, "Product Study of the Gas-Phase BrO-Initiated Oxidation of $Hg^0$: Evidence for Stable $Hg^{1+}$ Compounds", Environmental Science and Technology, 38(16); 4319-4326, Jul. 2, 2004.

\* cited by examiner

Figure 5a
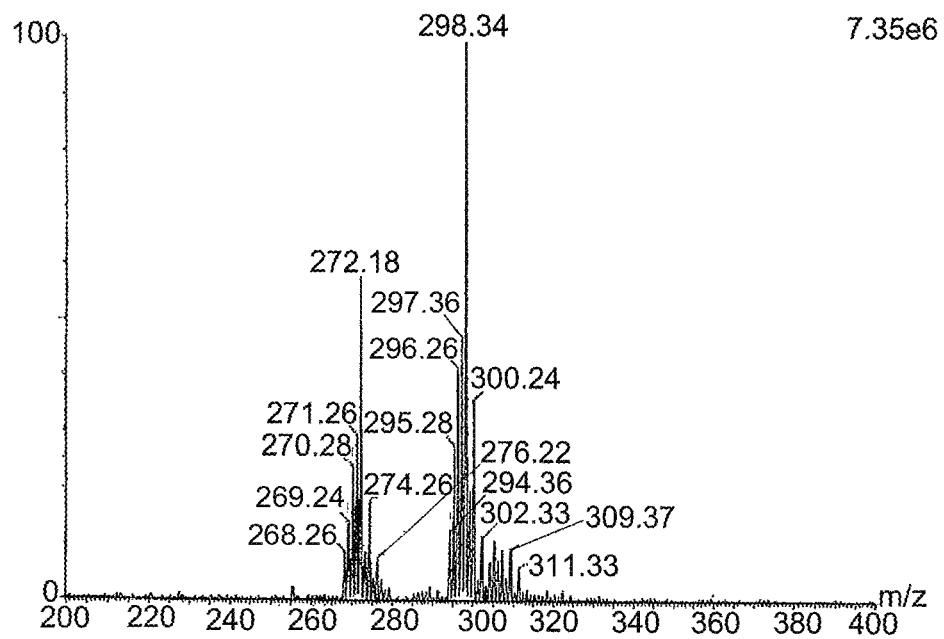
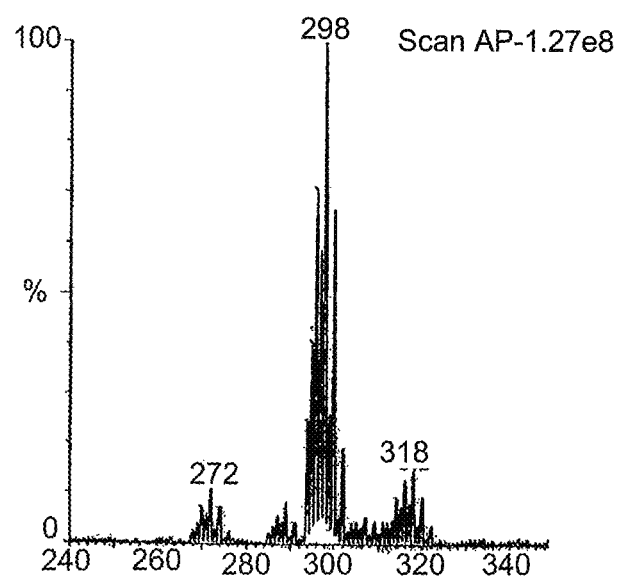
Figure 5b

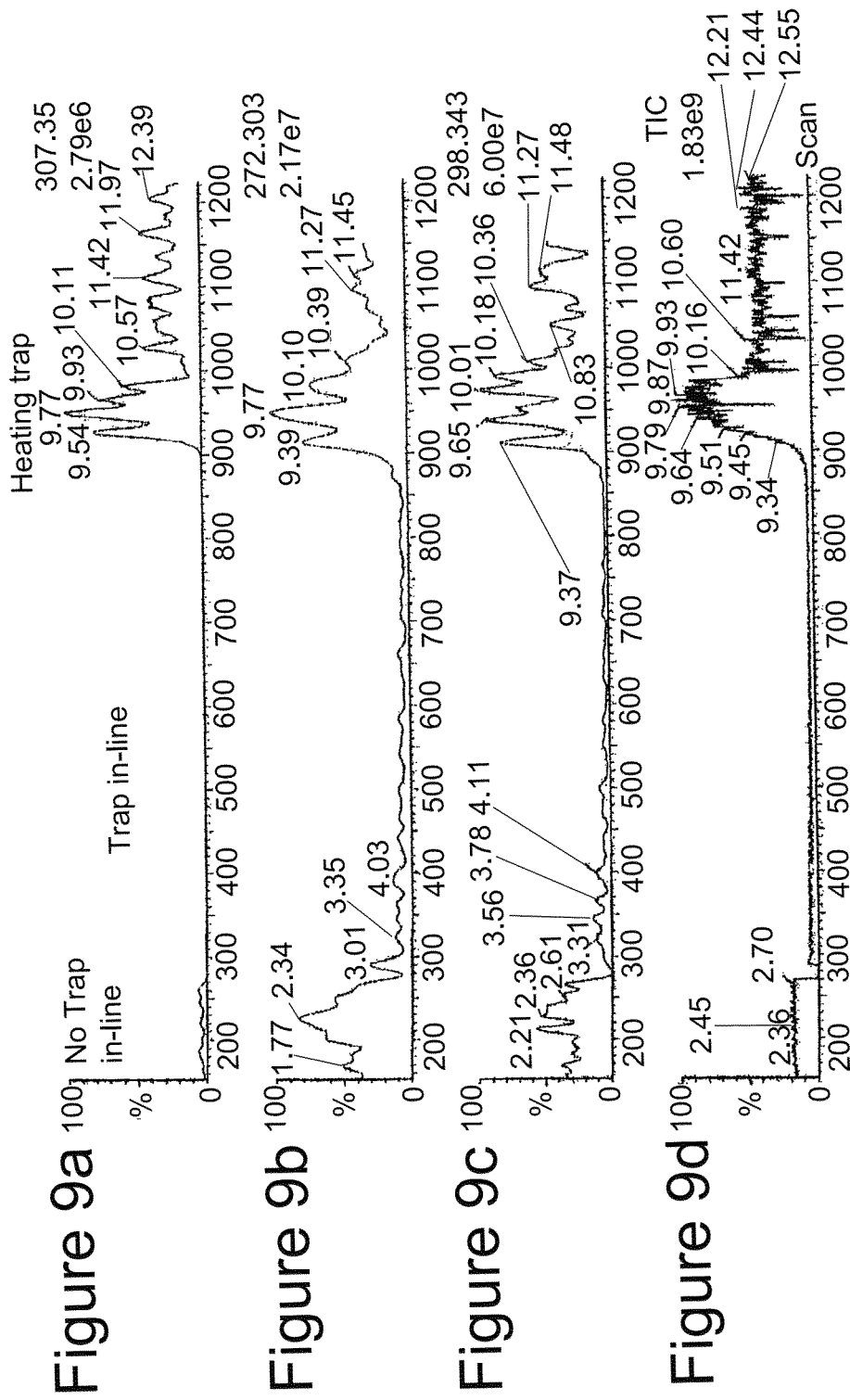

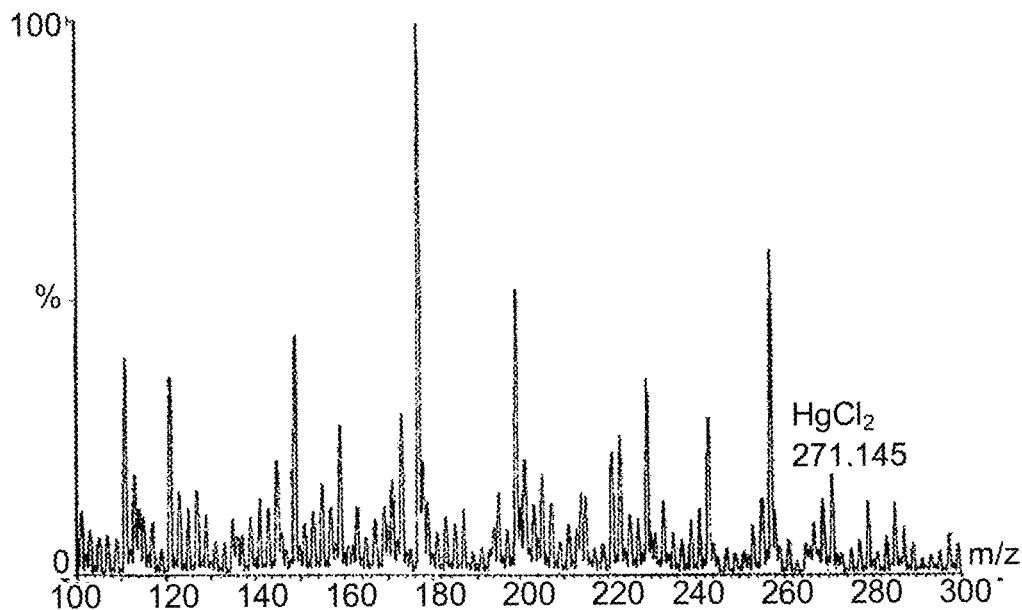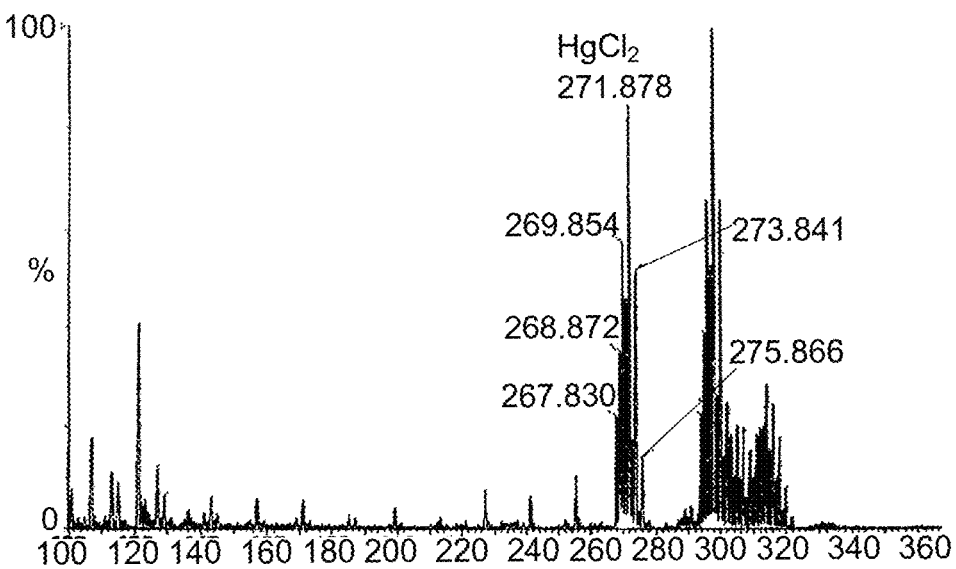
Figure 12b

METHOD AND SYSTEM FOR THE QUANTITATIVE CHEMICAL SPECIATION OF HEAVY METALS AND OTHER TOXIC POLLUTANTS

CROSS REFERENCE TO RELATED APPLICATIONS

This application is a continuation of U.S. patent application Ser. No. 13/391,093, filed Apr. 30, 2012, which is a U.S. National Phase of International Patent Application PCT/CA2010/001274, filed on Aug. 18, 2010, which claims the benefit of U.S. Provisional Patent Application Ser. No. 61/235,034 filed Aug. 19, 2009, which are all hereby incorporated by reference in their entireties.

FIELD OF THE INVENTION

The invention relates generally to methods, systems and portable devices for measuring quantitatively multiple species of heavy metals, including mercury or other toxic pollutants in air, and in the aqueous phase, including water, molten snow/ice, and rain.

BACKGROUND OF THE INVENTION

Mercury is the top-identified contaminant in the environment and has been identified as a toxic agent by international advisory boards. It is the one metal that is least effectively retained by emission controls, partly due to its high vapour pressure. Once emitted, mercury may be deposited by wet and dry processes to environmental surfaces. In its vapour form, mercury can be carried long distances on wind currents, staying in the atmosphere for long periods of time. Mercury can change from one form to another in the environment (FIG. 1). For example, some types of bacteria and fungi can change mercury into its most toxic form, methyl mercury. Methyl mercury tends to be bio-magnified, accumulating to some degree in all fish, but especially in predatory fish such as shark, swordfish and large tuna, as well as in marine mammals. Mercury is also leached from flooded soil at new hydroelectric dam sites, or from any flooded area. This process can add to mercury levels in freshwater aquatic food chains in those areas. The health effects of mercury exposure depend on its chemical form (elemental, inorganic or organic), the route of exposure (inhalation, ingestion or skin contact), and the level of exposure. Vapour from liquid elemental mercury and methyl mercury is more easily absorbed than inorganic mercury salts and can therefore cause more harm.

Therefore knowledge of the different forms or speciation of atmospheric mercury is crucial for predicting its deposition and understanding its biogeochemical cycling. Presently the current techniques provide information on elemental analysis and the chemical composition of mercury species cannot be determined in detail. Mercury speciation measurement is one of the most important challenges. The current inability to measure multiple mercury species constitutes a major gap in the understanding of mercury cycling and precludes adequate conclusions by scientists and policymakers alike [1]. Presently, existing analytic techniques for atmospheric mercury only provide information on (a) total mercury; (b) elemental mercury, (c) particulate mercury, and (d) an operationally (but not chemically) defined group called reactive gaseous mercury (RGM). The detailed chemical characterization of RGM is essential in understanding properties such as solubility, gas-to-particle partitioning, as well as processes such as biomagnification and bio-accumulation in aquatic systems. Currently, the major mercury detection systems include a gold trap used in connection with cold-vapour fluorescence units or atomic absorption units for mercury analysis. Using these techniques, one can obtain total mercury concentrations, as well as accurate elemental mercury concentrations. However, obtaining accurate concentration of mercury-containing molecular species is currently not possible. Therefore, there is a need for a method and device that identifies and quantifies the many different species of mercury in air and aqueous systems.

SUMMARY OF THE INVENTION

The present invention reduces the aforesaid difficulties and disadvantages. The present invention provides methods, systems and portable devices for the identification and quantification of mercury species and other metal species (e.g. heavy metal species) in air and in aqueous systems, as well as in ice and snow.

According to one aspect, the invention relates to a method for identifying and quantifying metal species, for example, heavy metal species (e.g. mercury (e.g. $HgBr_2$, $HgO$, $Hg(OH)_2$, $HgCl_2$, $CH_3HgCl$, and the like), lead, arsenic, cadmium, zinc, and the like), in a sample (e.g. air, water, snow, ice, and the like), comprising the steps of: a) collecting the sample onto a collection interface thereby concentrating an analyte; b) desorbing the analyte; and c) identifying and quantifying the analyte's content in metal species by atmospheric pressure soft ionization mass spectrometry.

In one embodiment, step (a) of the method of the invention comprises adsorbing the analyte onto the collection interface, e.g. by forming an amalgam, or by physical or physicochemical adsorption. In one embodiment, the collection interface of step (a) comprises particles, microparticles, nanoparticles, or beads coated with the same, as well as beads, wire, and the like, in a tube (e.g. glass, stainless steel, and the like). Examples of collection interfaces include, without limitation, gold particles, nanoparticles, gold-microparticle-coated glass beads (e.g. quartz beads), gold wire, sulphur-containing coated nano and microparticles, polysulfide-polysilanized glass beads (e.g. quartz beads), or uncoated glass beads (e.g. quartz, Pyrex™ and the like). The collection interface of step (a) may further comprise a heating option, such as a nichrome wire for controlling the temperature and for the desorbing step (b).

In another embodiment, step (a) comprises passing the sample through the collection interface at the flow rate of about 0.5 L/min to about 10 L/min, preferably about 0.8 L/min to about 5 L/min, more preferably about 0.8 L/min to about 1.5 L/min, most preferably about 1 L/min±0.20 L/min.

In another embodiment, the method further comprises passing the analyte from step (b) through a flow through a flow tube until it reaches the proximity of a detector of a mass spectrometer. In a further embodiment, the atmospheric pressure soft ionization mass spectrometry (APSI-MS) is atmospheric pressure chemical ionization mass spectrometry (APCI-MS). Soft ionization mass spectrometry (SI-MS) refers to a method in which the fractionation of ions are significantly reduced. SI-MS can be operated at various conditions including at atmospheric pressure. In one embodiment, the carrier gas for chemical ionization is nitrogen or isobutane-containing nitrogen, preferably nitrogen containing from about 0.01% to about 2% isobutane, from about 0.05% to about 1% isobutane, from about 0.05% to about 0.5% isobutane, from about 0.08% to about 0.2% isobutane, or about 0.1% isobutane.

In a yet another embodiment, all surfaces exposed to the analyte sample are inactivated or made of inactive material to prevent loss of analyte species. Examples of inactivation include halocarbon wax, silanization, and Teflon™ coating. Alternatively, some parts may be made out of an inactive material such as Teflon™ or glass covered Teflon™.

Another aspect of the invention relates to a system or apparatus for use in performing the method of the invention, the system comprising at least one collection interface as defined above, optionally including a heating option, an inlet end being optionally controlled by a flow valve, and optionally containing a filter or multistage size-aggregated filters. The system also further comprises a flow tube connecting an outlet end of the collection interface to an inlet of an atmospheric pressure soft ionization mass spectrometer detector such as (atmospheric pressure) chemical ionization, or electrospray options. The system comprises inactivated inner walls for preventing loss of analyte species, or alternatively comprises means for doing so.

In yet another aspect, the invention relates to a method for modifying a MS apparatus in order to perform the method of the invention, such method comprising inactivating the surfaces contacting the sample analyte, such as flow tubes, inlet walls, and interior of MS. The method further comprise adding a concentration or collection interface as defined above, and reducing the dead volume inside the injector port of the MS apparatus.

In a further aspect the invention relates to a portable device or a kit for modifying an existing MS apparatus in order to perform the method of the invention, the kit comprising a one or more collection interface, flow valve(s) and tube(s) for connecting to an interface inlet, flow tube(s) for connecting from an interface outlet to an APSI-MS detector inlet, means or instructions for inactivating/passivating inner surfaces of the device and APSI-MS, and means for reducing the dead volume inside the injector port of the MS apparatus.

BRIEF DESCRIPTION OF THE DRAWINGS

Further aspects and advantages of the present invention will become better understood with reference to the description in association with the following drawings in which:

FIGS. 5a and 5b shows a comparison of $HgCl_2$ mass spectra obtained with AC-APCI-MS (a) and DC-APCI-MS (b) with isobutane as a chemical ionization (CI) gas.

FIGS. 9a to 9d are MS spectra showing trapping of $HgCl_2$ on quartz-beads, followed by thermal desorption.

FIG. 12b shows the APCI-MS analysis of ~50 nmol $HgCl_2$ (in methanol).

DETAILED DESCRIPTION OF THE INVENTION

Figure 1:
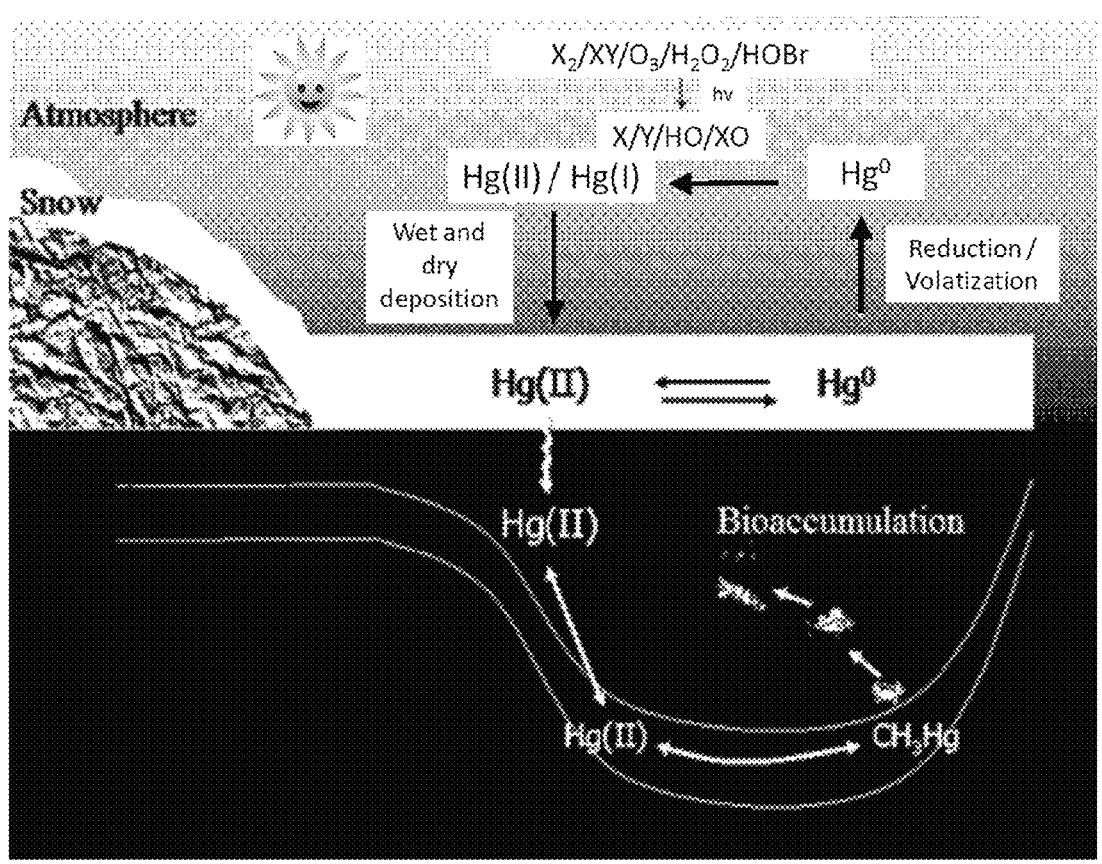
FIG. 1 is a schematic view of mercury in the environment.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", "having", "containing", or "involving" and variations thereof herein, is meant to encompass the items listed thereafter as well as, optionally, additional items. In the following description, the same numerical references refer to similar elements. In the drawings, like reference characters designate like or similar parts.

A method of identifying and quantifying metal species in air or liquid samples according to an embodiment of the invention is described herein with reference to mercury species in air and liquid samples. However, it will be appreciated that the present invention can also be applied to metals other than mercury.

Figure 2:
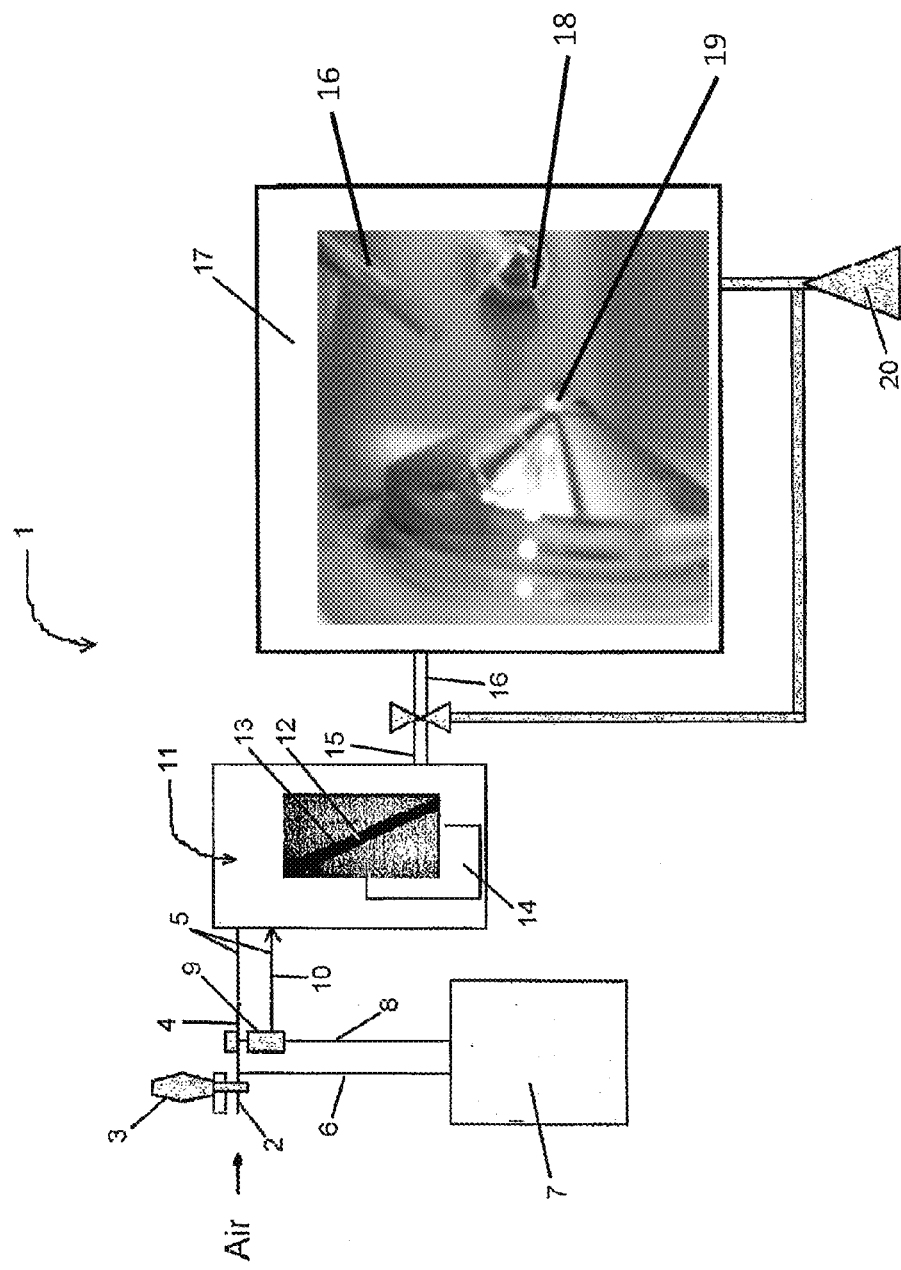
FIG. 2 is a simplified schematic of the device of the present invention.

An example of a system to be used in the method of the invention is shown in FIG. 2 as a simplified representation. In this system (1), for example, air is passed through a sample inlet (2), its flow being regulated by a meter (3). The air sample (4) may go directly through to the interface inlet (5) or may as total mercury (6) go to the Cold Vapor Atomic Fluorescence Spectrometer (7) (CVAFS), where total mercury is measured. The sample then comes out as size-aggregated particulate mercury (8) to pass through a size-aggregated filter(s) (9) to separate aerosols, exiting as a sample (10) containing gaseous mercury compounds, the particles having been collected on the filter(s).

Analyte from either samples coming out of the interface inlets (5) are then collected on an interface (11) comprising particles (12) inside a flow tube (13). The analyte is collected and concentrated on the particles either by simple physical or physicochemical adsorption or by the formation of an amalgam, depending on the particles used. Optionally a heating option (14) is fitted around the collection interface to help desorption of the analyte.

After desorption, the analyte comes out the interface outlet (15) to the inlet (16) of the mass spectrometer (17). The inlet (16) is situated proximate to the ionization electrode (18) and charged collector to MS (19) to reduce the dead volume. The pumping unit (20) used in the method of the invention is also shown in FIG. 2.

Figure 3:
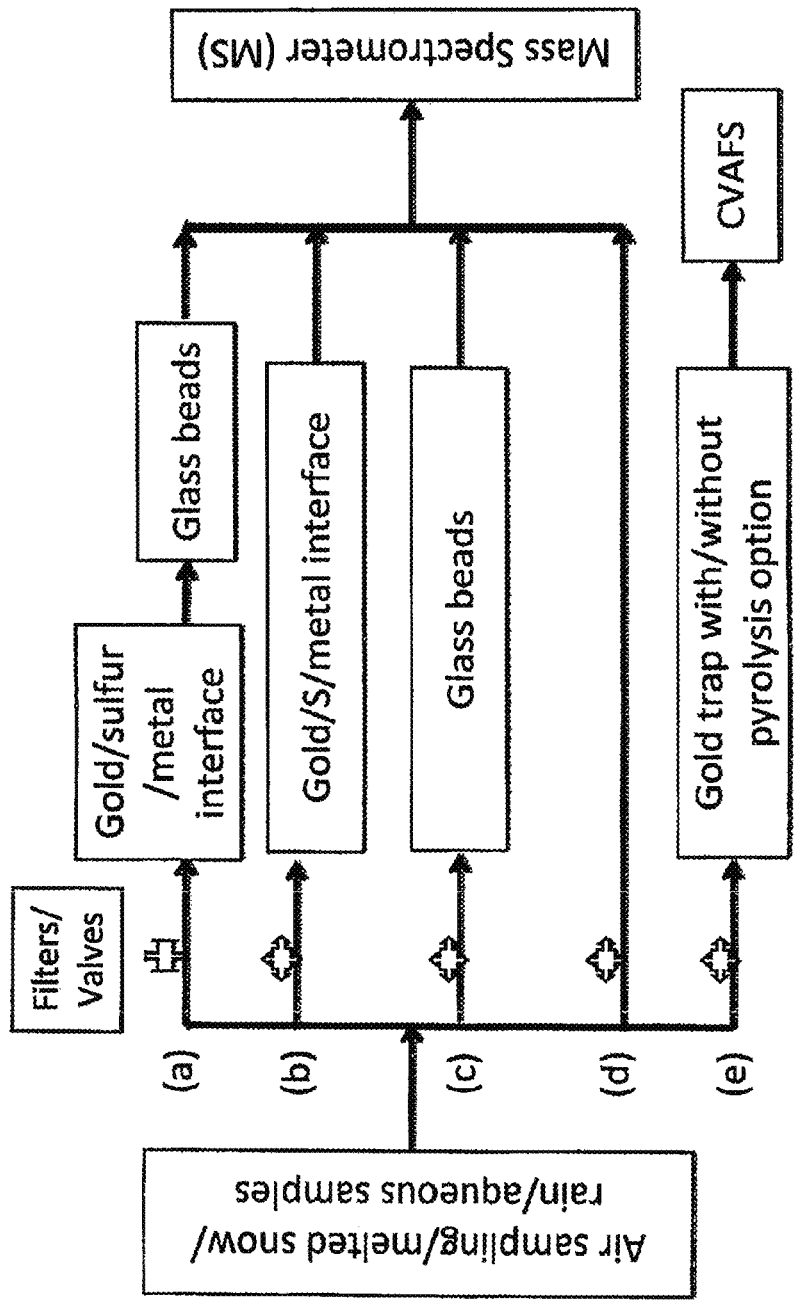
FIG. 3 is a simplified schematic representation of an exemplary configuration for mercury analysis.

Another schematic representation of a system for use in the method of the invention is shown in FIG. 3, where multiple types of interfaces and control valves are used. This way, samples going through path (a) will be collected on both a mercury adsorption interface (e.g. gold, metals and metal oxides, as well as sulfur containing compounds) as well as glass beads to facilitate desorption to mass spectrometry; samples going through path (b) will be collected on a mercury adsorption interface alone; samples going through path (c) will be collected on a glass bead interface (to adsorb all adsorbing pollutants in diluents fluid); samples going through path (d) are injected directly without being collected; and samples going through path (e) are adsorbed on a gold interface with and without pyrolysis using a cold-vapor fluorescence detector (CVAFS) as an analytical comparison, and thus total mercury, elemental mercury particulate and some oxidized mercury data can be obtained. It is of note that the CVAFS does not provide adequate detailed chemical speciation for oxidized mercury species that mass spectrometry options can provide. Each sample path is controlled via an independent valve such that only one sample is analyzed at the time. Results of the analysis through the mass spectrometer for each individual path are compiled in the computer system to identify and quantify each mercury species present in the original air or water sample.

The Mass Spectrometer used for the method of the invention is, preferably, a modified atmospheric pressure soft ionization mass spectrometer (APSI-MS). The soft ionization mass spectrometer can be an atmospheric pressure chemical ionization mass spectrometer (APCI-MS) for air samples or an electrospray ionization mass spectrometer (EI-MS), preferably an atmospheric pressure chemical ionization mass spectrometer (APCI-MS).

The collection interface for use in the methods and systems of the invention generally comprises particles, microparticles, nanoparticles, or beads coated with the same, as well as beads, wire, and the like, in a tube (e.g. glass, stainless steel, and the like). For example, the collection interface comprises, without limitation, gold particles (e.g. microparticles, nanoparticles, and the like), gold-particles-coated beads or wire (e.g. glass beads such as quartz beads, or stainless steel, iron or copper beads or wire), gold wire, polysulfide-polysilanized beads or wire (e.g. glass beads such as quartz beads, or stainless steel, iron or copper beads or wire), uncoated glass beads (e.g. quartz, Pyrex™ and the like), or a combination thereof.

In one example, the use of gold nanoparticles in the interface increases the surface area significantly and thereby improves the sensitivity. Both gold and sulfur coated metal nanoparticles can be used as well as pure gold nanoparticles. These molecules provide strong chemical attraction with mercury compounds and hence are adequate for binding.

Surprisingly, the use of uncoated glass beads, such as quartz beads, also provides for a good analyte collection and concentration in the interface, as well as a smooth desorption with negligible or no poisoning of the sample.

The use of a mercury adsorbing interface followed by a glass beads interface such as path (a) of FIG. 3, will particularly facilitate desorption of mercury compounds and differential adsorption of gaseous elemental mercury and gaseous oxidized mercury.

The heating option adapted for the collection interface may be, for example, a nichrome wire, or any other controllable heating means known to the skilled in the art.

The following modification to the APSI-MS have also been made to the system: the inlet compartment, the flow system and all connection tubing and interface walls have been coated with a coating or deactivation agent, or replaced by unreactive equivalent parts to decrease the losses and potential side reaction of mercury compounds inside the instrument itself. The dead-volume inside the injector inlet of the APSE-MS has been decreased to increase the sensitivity of the instrument. This technique is recyclable, and is designed to be environmentally benign.

From one aspect, the invention consists of a portable flow-system device which includes a collection interface, e.g. gold/sulphur-containing nanoparticle-based substrate or glass beads for analyte capture/adsorption. The device can be directly mounted on a mass spectrometer to obtain both qualitative and quantitative chemical species data for mercury in an air stream. Alternatively, the device can be used to collect samples directly from the air stream exiting a plant stack then be removed and attached to a mass spectrometer for sample analysis. Optionally, the portable device comprises multiple interfaces and valves as described above and/or multistage filter, for those interested in particulate chemical speciation analysis.

Advantageously, the present invention provides quantification for various mercury species including compounds such as $HgBr_2$, $HgO$, $Hg(OH)_2$, $HgCl_2$ in gas phase and condensed phases (e.g., air, aerosols, clouds, ice, snow and water). None of the existing commercial techniques leads to detailed and quantifiable mercury speciation under atmospheric conditions. The time resolution of the present invention is superior or comparable with all current techniques that do not provide such chemical speciation.

The portability of the device, together with its unique enablement of mercury speciation (both qualitative and quantitative), points to applications ranging from coal-based electricity generating plants to refineries (oil, aluminum), through to hydro-electric utilities.

EXAMPLES

Example 1

Preparation of the System a. Preparation of Gold Nanoparticle-Coated Fiber and Trap Single layer Au-nanoparticle surfaces are coated onto stainless-steel interface and/or a wire for mercury capture. The process begins by cleaning the stainless-steel wire with a 3:1 mixture of concentrated $H_2SO_4$ and 30% $H_2O_2$, both to remove trace organics and other contaminants and to increase the number of pendant oxygen atoms available for silanization on the surface. The cleaned wire was then immersed for two minutes in a solution containing 60 µL of 3-(aminopropyl)-trimethoxysilane (APTMS) dissolved in 15 mL of a 3:1 mix of 18.2 MΩ water and ethanol. After silanization, loose silanes were removed from the surface by rinsing with ethanol, and the wire/filter/trap was blown-dry with UHP $N_2$ gas. The APTMS was allowed to cure at room temperature for several hours before continuing the SPME preparation.

Once the APTMS-covered wire had cured, it was immersed in a gold nanoparticle colloidal solution for 15 minutes, under agitation. The electrostatic attraction between pendant amines on the silane film and gold nanoparticles results in a fine coating of gold on the surface.

Figure 4:
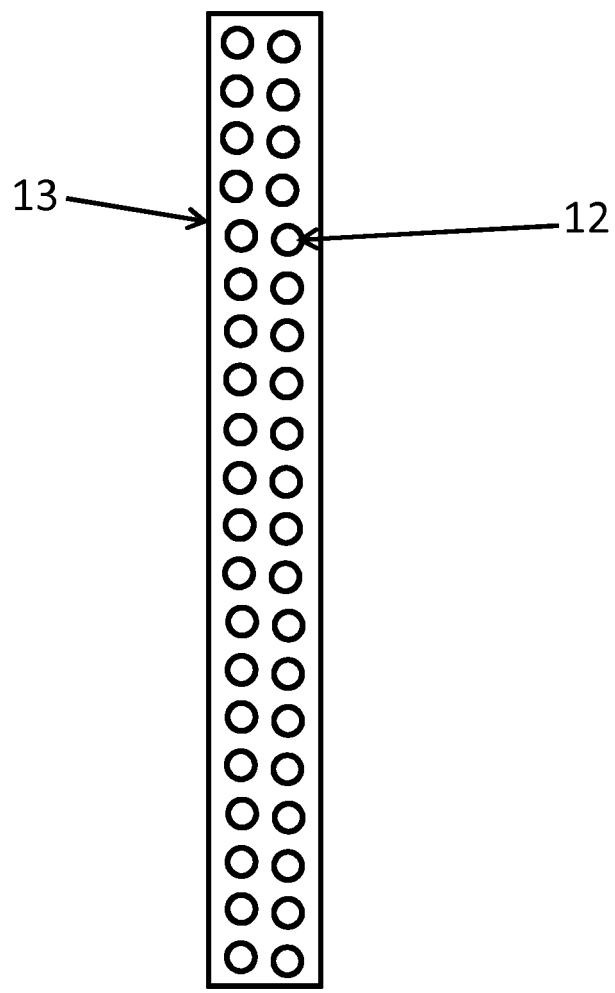
FIG. 4 is an example of a nanoparticle-coated interface produced.

In addition to pure gold, we have deployed traps using elemental sulfur as well as coated iron and copper nanoparticles. 2 g of 1:1 elemental sulphur: support were used. Sorbent was preconditioned under $N_2$ at 400° C. for 6 hours. Bis-[3-(triethoxysilyl) propyl]tetra-sulfide] ("S4") was also coated onto copper-doped iron or copper oxide nanoparticles. An example of a collection interface is shown in FIG. 4.

b. Deactivation of all Surfaces (Inlet, Flow Tube, Internal MS Surfaces, Connectors)

Inactivation of all surfaces exposed to analyte sample, that is, walls of inlet, flow tube, interior of MS, was performed to preclude the loss of analyte species prior to mass-based separation of species. The interior wall of the flow tube, the interface containing nanoparticles (FIG. 4), the connections to the MS as well as the interior of the inlet compartment of the mass spectrometer were deactivated by means of silylation and halocarbon wax coating techniques that were described in detail elsewhere [2, 3]. This reduces the mercury loss on the surfaces, while also reducing the undesired side reactions which interfere with accurate quantification of the mercury species.

More specifically regarding the APCI-MS inlet, the stainless-steel-and-glass APCI-MS inlet was first replaced with a 10 mL Teflon™ cell to ameliorate analyte retention in the ionization source, by removing scavenging surfaces and by focussing the analyte-rich gas stream into the ionizing corona surrounding the high-voltage discharge pin in the APCI source. However, static build-up was observed on the inner surfaces of the Teflon™ cell during operation of the high-voltage discharge pin, resulting in deflection of the surrounding corona out of the path of the gas stream and complete loss of APCI-signal.

The Teflon™ cover of the cell may be replaced with an analogous cover made of quartz. However, this has the potential to scavenge analyte during analysis. In fact, using this quartz cover, the APCI signal was inconsistent and the corona was prone to disappear if the discharge pin were not held at maximum voltage (4 kV).

We note that the Teflon™ cell (with glass cover) does improve instrument sensitivity by an order of magnitude, from a S/N of ~10 for $HgCl_2$ with the original APCI configuration to a S/N of ~100 when using the Teflon™ cell. The static electricity problem was solved through the application of AC current to the discharge pin, as described below.

Surface passivation of the original APCI inlet with halocarbon wax or by silanization were tested. Halocarbon wax required only dissolution in solvents such as acetone for application onto the surfaces of the APCI inlet, followed by evaporation of the acetone overnight at 150° C. A disadvantage of the halocarbon wax is the outgas of chlorine gas into the APCI source, resulting in the formation of $Cl^-$ ions which complex with molecular ions produced from the analyte, resulting in mixed halides (e.g. $[HgBr_2Cl]^-$) which could prevent the positive identification of the specific chemical form of atmospheric oxidized mercury species.

Metal and glass surfaces in the APCI source were silanized with dichloromethylsilane (DCDMS) by immersion overnight in a 5% DCDMS in ethanol solution followed by curing for several hours at 150° C. Initial results indicated that there was little or no change in scavenging of oxidized mercury by the silanized-APCI inlet (vs. non-silanized inlet).

c. Modifying Coronal Discharge

As mentioned above, the APCI-signal using the glass-covered Teflon™ cell was less consistent and prone to shortage. To prevent static build-up, the DC voltage source of the APCI-MS instrument was replaced with a custom-made 60 Hz AC source that supplies the same voltage range. Negative static that would normally accumulate on the Teflon™ surfaces and deflect the negative ion corona is instead neutralized during the positive cycle of the discharge pin. Initial tests with isobutane and an AC voltage applied to the discharge pin show retention of the analyte as both molecular ion (and the $[M+C_2H_2]^-$ ion with somewhat lower signal when compared to the DC voltage APCI-MS ($7\times10^6$ cts vs. $3\times10^8$ cts)). This may be due to the incomplete conversion of the analyte to the acetylene complex seen in DC-APCI-MS. Regardless, the S/N ratio for both methods is comparable (S/N~1000). As an added benefit, the glass cover may be replaced with its Teflon™ counterpart when using AC-APCI-MS, removing the last potential surface for scavenging of analyte introduced into the APCI source. FIG. 5 shows a comparison of $HgCl_2$ mass spectra obtained with AC-APCI-MS (a) and DC-APCI-MS (d) with isobutane as a chemical ionization gas. The larger signal for DC-APCI-MS may reflect a more effective conversion of the molecular ion to the $[M+C_2H_2]^-$ ion (m/z=298).

d. Decreasing the Dead Volume Inside the Injector Port

Figure 6:
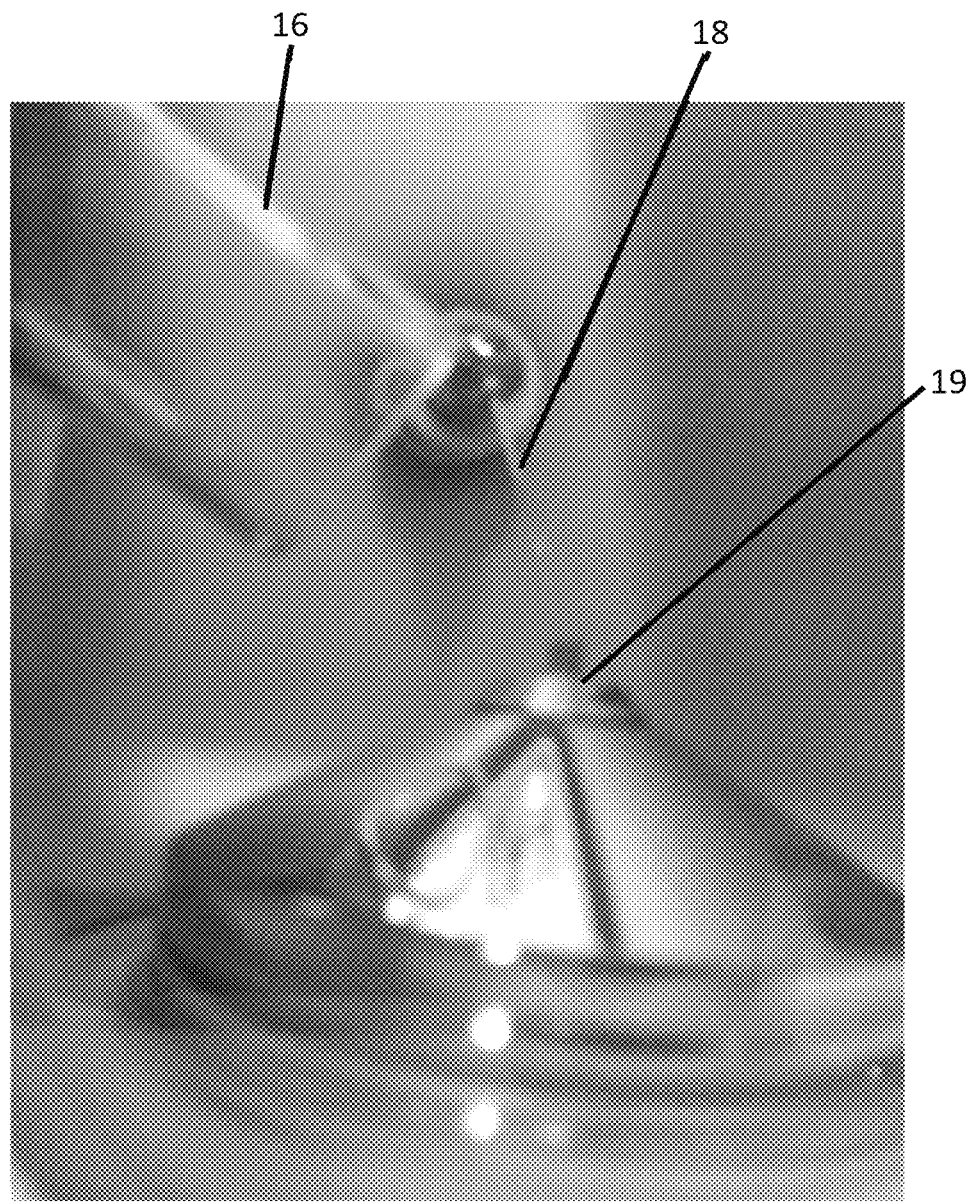
FIG. 6 shows the APSI-MS source for gas analysis.

Significantly decreasing the dead volume inside the inlet enables identification of different mercury species, as it minimizes mercury loss inside the inlet. In order to increase the sensitivity of the mass spectrometry signals for mercury containing compounds, we have used a deactivated tube bringing the flow to the vicinity of charged collector to mass spectrometer, and thus reducing the dead volume (see FIG. 6).

e. Initial Systems Response Test

Figure 7:
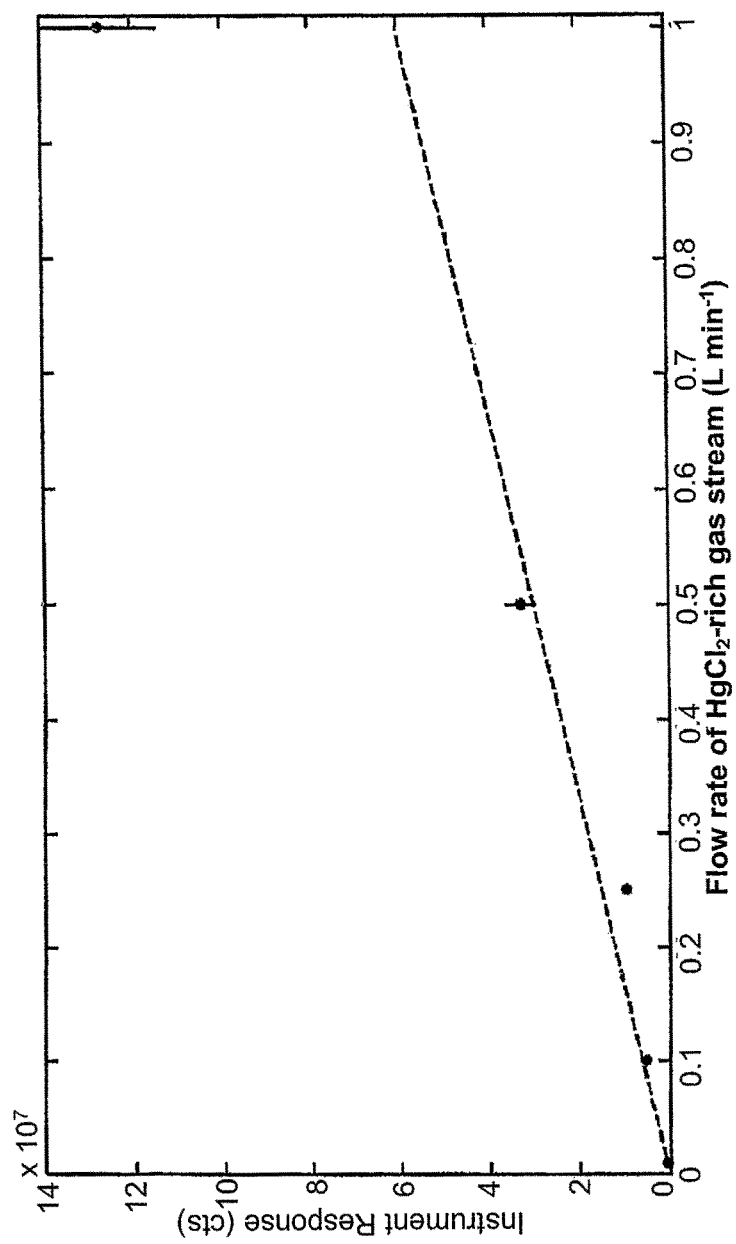
FIG. 7 is a graph showing instrument sensitivity to a $HgCl_2$-saturated gas stream as a function of the gas flow rate.

To test the sensitivity of the APCI-MS instrument to $HgX_2$, isobutane chemical ionization (CI) gas was passed through the $HgCl_2$-saturated flask to the glass-covered Teflon™ cell and APCI-source. The flow rate of the CI gas was modulated to increase/decrease the quantity of analyte entering the cell per unit time. The response of the instrument was roughly linear up to 0.5 L/min, after which the sensitivity of the instrument appeared to increase significantly (FIG. 7).

The observed nonlinearity of the instrument may result from the small volume of the Teflon™ cell (10 mL) combined with the critical-flow rate (~0.8 L/min) across the charged cone used to collect ions into the mass spectrometer for detection. Below this critical flow rate, the evacuated section behind the charged cone may reduce the internal pressure of the Teflon™ cell, lowering the ion density in the corona and decreasing the ionization of the analyte. Increasing the flow rate to ~0.8 L/min or above restored the instrument to a "true" APCI-MS analysis. All further analyses were held at 1 L/min to retain the high sensitivity to $HgX_2$ observed in this study. Also of note is that a signal of $10^8$ for a $HgCl_2$-saturated gas stream at 1 L/min with a baseline noise of $10^4$ cts, provides a method detection limit of ~7 pg $HgCl_2$. Thus, for optimal analysis, the oxidized mercury from at least 1-2 $m^3$ of air should be collected for detection and quantification.

Example 2

Analyte Collection for Sample a. Example of Collection Using a Sampling Flask as an Interface Gold and/or sulfur nanoparticle-coated surfaces (e.g. Fe/Au) were preconditioned for several minutes under vacuum at a temperature of ca. 360° C. before insertion into a ~2 L air sampling flask. The sampling flask, as well as all FEP tubing up-flow of the flask, was washed several times with 1M nitric acid and 18.2 MΩ water. Air was passed through the air sampling flask at ca. 18 L per minute for a total time of 14-19 hours. In one extraction, a 0.45 μm Teflon™ filter was attached at the sample line inlet to prevent particulate mercury from entering the sample line.

b. Analyte Pre-Concentration from Air

A series of physical and physicochemical traps for the collection of measureable quantities of oxidized mercury from large volumes of air have been developed. For example, traps included pieces of 10 cm long 6 mm diameter glass tubing containing gold-microparticle-coated quartz beads, uncoated quartz beads, gold wire, or polysulfide-silanized quartz beads, as well as a 10 cm long 6 mm diameter empty stainless-steel tube. Nichrome wire was wrapped around each trap to provide an easily-controllable heating source for desorption of analytes into the APCI-MS.

Figures 8A, 8B:
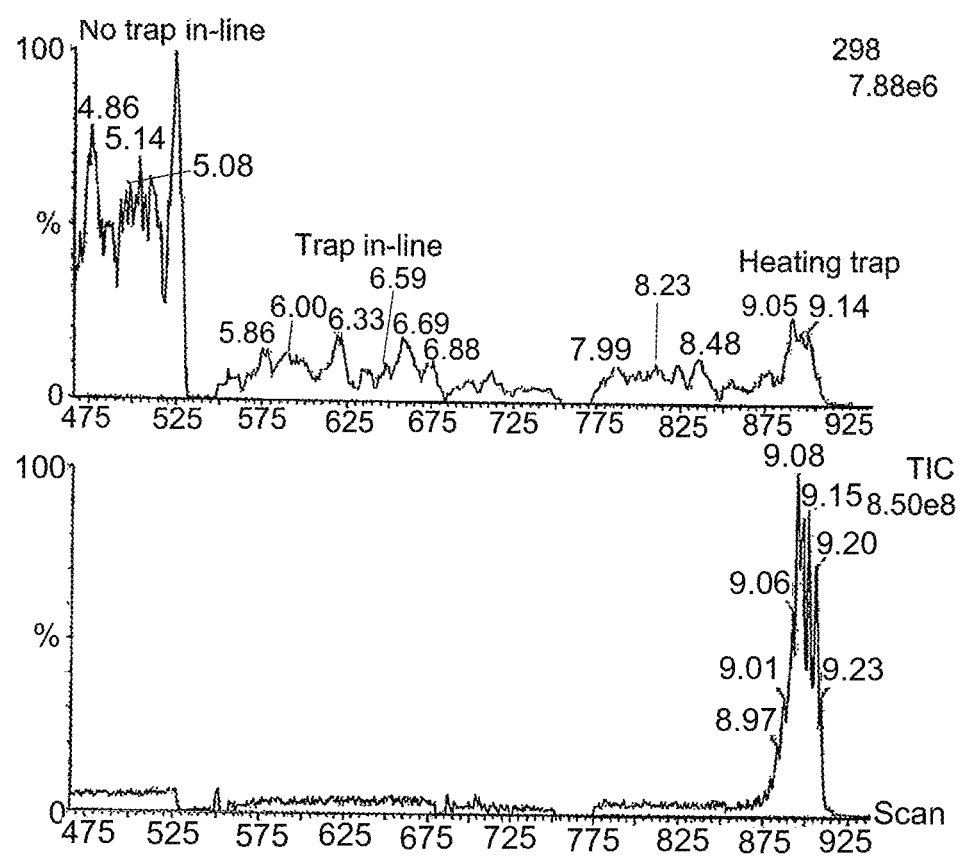
FIGS. 8a and 8b are MS spectra showing collection of $HgCl_2$ onto gold microparticles, and thermal desorption.

Gold-microparticle-coated glass beads were capable of removing approximately 80% of incoming $HgCl_2$ in a saturated gas stream (FIG. 8). Initial desorption tests indicated that the $HgCl_2$ decomposed at temperatures necessary for destabilization of the mercury-gold amalgam, resulting in a lower yield from the trap. Total ion count (TIC) for the mass spectrum is shown in the lower panel of FIG. 8. The trapping efficiency of $HgCl_2$ is approximately 80%.

In another example, uncoated glass beads collected $HgCl_2$ from a 1 L/min stream of $HgCl_2$-saturated gas. The collected $HgCl_2$ was recovered during thermal desorption, as both $[HgCl_2]^-$ and $[HgCl_2+C_2H_2]^-$. The desorption peak observed for mass 307 ($[HgCl_3]^-$) upon heating was not observed previously in the run, and may indicate some thermal decomposition may be occurring. Desorption as lower temperature may reduce this phenomenon. $HgCl_2$ collection was in the order of 90%, and was recovered in the detector as both the molecular ion and acetylene complex (see FIG. 9).

Also, as the collection of $HgX_2$ by uncoated glass beads is by physical adsorption only (as opposed to the mercury amalgamation that occurs with gold), mercury species may in competition with other low volatility compounds in air. Collection of $HgX_2$ at elevated temperature (~50° C.) may reduce the competitive adsorption of other compounds by the trap.

Example 3

Figure 10:
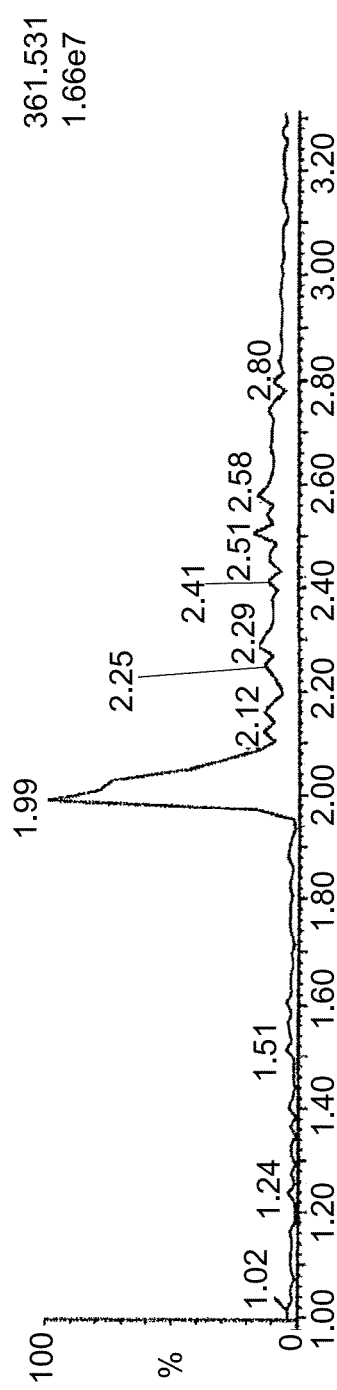
FIG. 10 is an example of the desorption of $HgBr_2$ collected from air using gold nanoparticles exposed to ambient air for 14 hours. Nitrogen was used as a reagent and carrier gas.

Calibration and Analysis a. APCI-MS Analysis of Mercury Species Extracted from Air Mercuric halides collected onto gold nanoparticles-coated fibers and traps were desorbed directly into the source of an atmospheric pressure chemical ionization mass spectrometer (APCI-MS) for detection. APCI-MS analysis of mercury halides is performed in negative mode (i.e. detection of negative ions only). The APCI-MS inlet accommodates both the fiber and a $N_2$ carrier gas that flows around the outer tubing of the fiber at a rate of 0.3-3 L/min. Initially, the inlet is kept isothermal at 50° C. while the fiber is exposed to the gas stream. No gases are observed to desorb from the fiber/trap at this temperature. When the instrument baseline is stable, the inlet is ramped to 360-375° C. over the course of several seconds. The $HgCl_2$ and $HgBr_2$-gold amalgams destabilize in the temperature range of 300-330° C., resulting in a peak whose area can be integrated for quantification similar to the chromatograms obtained by gas chromatography. FIG. 10 is an example of the desorption of $HgBr_2$ collected from air using gold nanoparticles.

The APCI-MS normally utilizes nitrogen as a reagent gas to ionize analytes in the corona discharge in the ion source. Excess energy after ionization of mercury halides results in fragmentation of the molecular ions and formation of mixed halides such as $HgBr_2Cl$. This prevents direct identification of the chemical species of mercury collected onto the SPME fiber. An alternative reagent gas is isobutane, which preserves molecular ions through complexation as $[M+26\ ]^-$. The negative mode APCI-MS analysis of isobutane shows the presence of a fraction at m/z=26, which is presumably $C_2H_2^-$, although tandem MS investigation of this mass does not provide solid evidence of its identity. Other carrier gases can be used to optimize the quantification of different mercury species.

Isobutane to replace nitrogen as the chemical ionization (CI) gas was a first choice, as it: 1) transfers less energy to the analyte, resulting in a "softer" ionization (i.e. less fragmentation) than nitrogen; 2) scavenges halide ions that may be produced by analyte fragmentation, preventing unwanted ion complexation; and 3) complexes with the molecular ion (M) in a consistent manner to form a $[M+C_2H_2]^-$ ion. APCI analysis with isobutane was initially performed at high concentrations of CI gas (>1% isobutane in nitrogen) but tailing from the large peak at m/z=58 (isobutane) was significantly present in the baseline in the region of interest for mercury halides (m/z=200-500).

Figure 11:
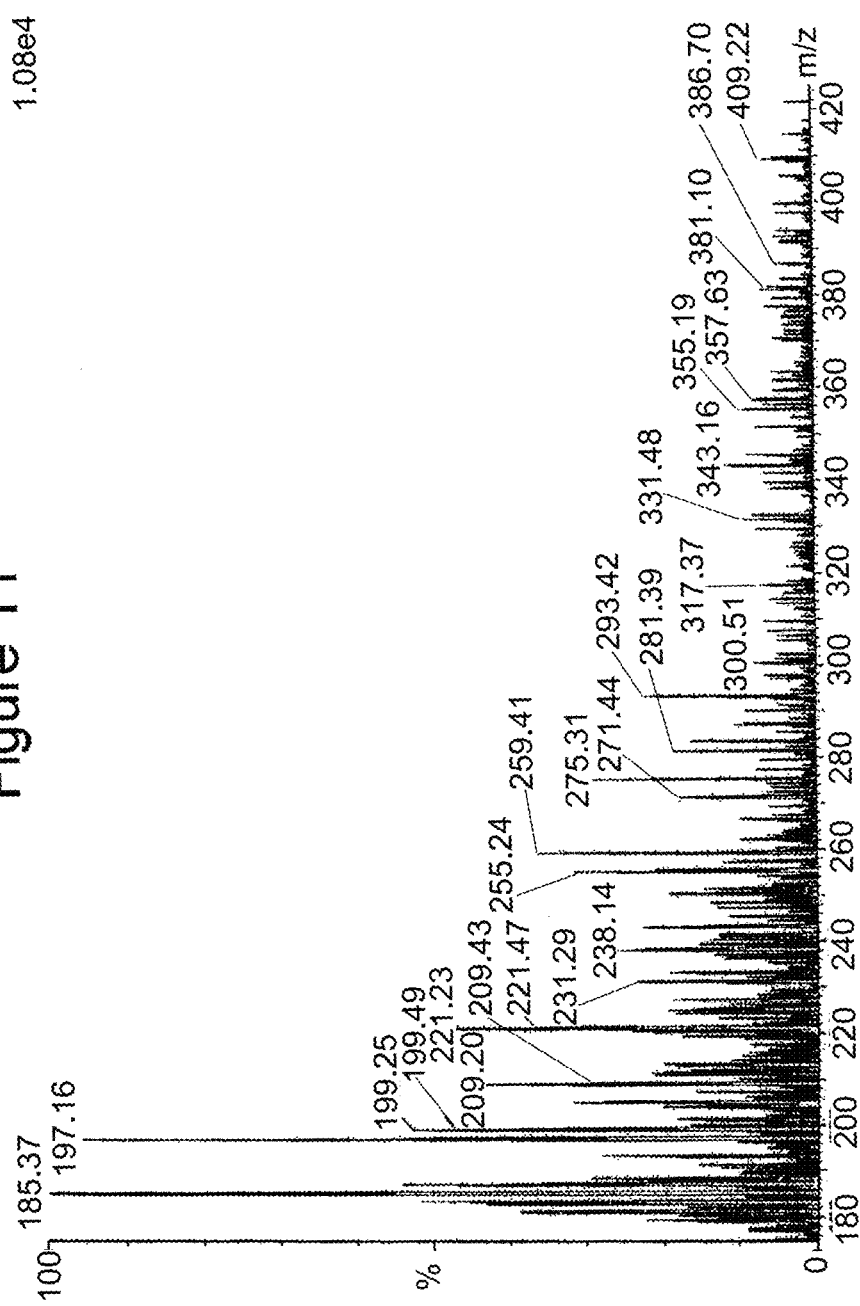
FIG. 11 shows a blank of APCI-MS with 0.1% isobutane in nitrogen as the chemical ionization (CI) gas.

For determining the optimal isobutene concentration, UHP nitrogen was passed at 2 L/min through a 3 L glass flask containing 1 atm of 100% isobutane into a $HgCl_2$ source to the APCI-MS while monitoring the mass spectrum at m/z=200-500. Under these conditions, the baseline decreased by roughly a factor of 10 (~$2\times10^5$ cts to ~$1\times10^4$ cts) in the first 15 minutes after the flask was opened, suggesting that decreasing the concentration of isobutane to roughly 50 ppm would improve the detection limit for $HgX_2$ significantly. Between 15 minutes and 30 minutes the baseline remained fairly constant, but the signal for $HgCl_2$ began to decrease as fragmentation by nitrogen increased. Operate with a relatively high concentration of isobutane (0.1% in nitrogen) was then used to ensure complete fragmentation while allowing the freedom to dilute down with UHP nitrogen to control the baseline intensity. At this concentration the tailing from isobutane may still be observed, but the total baseline intensity is still low (see FIG. 11).

b. Calibration

Gold and other nanoparticle-coated metal fibers were calibrated by insertion into flasks containing the pure compounds of interest, for e.g. a single mercuric halide salt, either $HgCl_2$ or $HgBr_2$, under a 1 atmosphere nitrogen headspace. At the temperatures of the laboratory, the headspaces of these flasks contained on the order of pmol $HgX_2$ per $m^3$ of gas. Au-nanoparticle fibers/traps were exposed to the standard headspace for a period of time consistent with respective air extractions. The fibers are then removed and stored in dry ice until analysis by APCI-MS, analogous to air extractions.

c. Calculation of Quantitative Results & Calibration and Determination of Concentration The quantification of mercuric halides, $HgX_2$ (X=Br, Cl, etc.) in whole-air samples is based on the instrument response to known quantities of pure analyte (i.e. standards) treated in an identical manner to the sample. For this method, this entails passing a gas with a known concentration of $HgX_2$ through a gold trap for collection, followed by thermal desorption into the atmospheric pressure chemical ionization mass spectrometer (APCI-MS) for detection. Ideally, this standard gas would be passed through the gold trap for a length of time equivalent to the sample collection, such that sample concentrations can be directly determined from the relative instrument responses. However, the long extraction times for whole-air samples make this method inconvenient for high-temporal-resolution atmospheric monitoring; a more accessible method of calibration would focus on absolute calibration of molar quantities of analyte introduced to the APCI-MS. Once the absolute quantity of analyte desorbed from a trap is known, the total volume of air passed through the trap and the trap collection efficiency may be used to accurately determine the original concentration in a whole-air sample.

Absolute calibration of the APCI-MS may be accomplished in several manners. In the first, a known quantity of gas containing a known concentration of $HgX_2$ is injected into an analyte-free gas stream that enters the instrument. Varying the quantity of gas injected results in the creation of a calibration curve that relates instrument response to the molar quantity of analyte introduced to the instrument. A second calibration method, that more closely follows the whole-air sampling routine, involves the passing of a known flux of $HgX_2$ standard through the gold trap used for sampling, in order to collect a known quantity of analyte in a short period of time. The flow rate may be adjusted using a flow meter and needle valve up-flow of the standard flask. The standard flask would consist of a multiple-stopcock-fitted glass flask containing solid crystals of the analyte under a nitrogen headspace. The quantity of analyte exiting the flask over time is determined by the flow rate of nitrogen passing through the flask and the vapour pressure of analyte in the flask's headspace. After collection on the trap, the standard is thermally-desorbed into the instrument for detection. Varying the flow rate or the collection time, or mixing the standard stream with another stream of analyte-free nitrogen, can all be used to alter the quantity of analyte introduced into the instrument for calibration. As an added benefit, the collection efficiency of the trap may be directly determined by setting the standard flask and trap in-line with the instrument during standard concentration on the trap, measuring the quantity of analyte that passes through the trap to the instrument, if any.

d. Particulate Separation and Quantification

The flow tube inlets can be operated with and without Teflon™ filters with diameters ranging from 0.1 micron to 2 microns. Hence the setup is used for identification of mercury compounds in the gas phase and particulate manner.

e. Usage of Both Positive and Negative Ion Mass Spectrometry

Figure 12A:
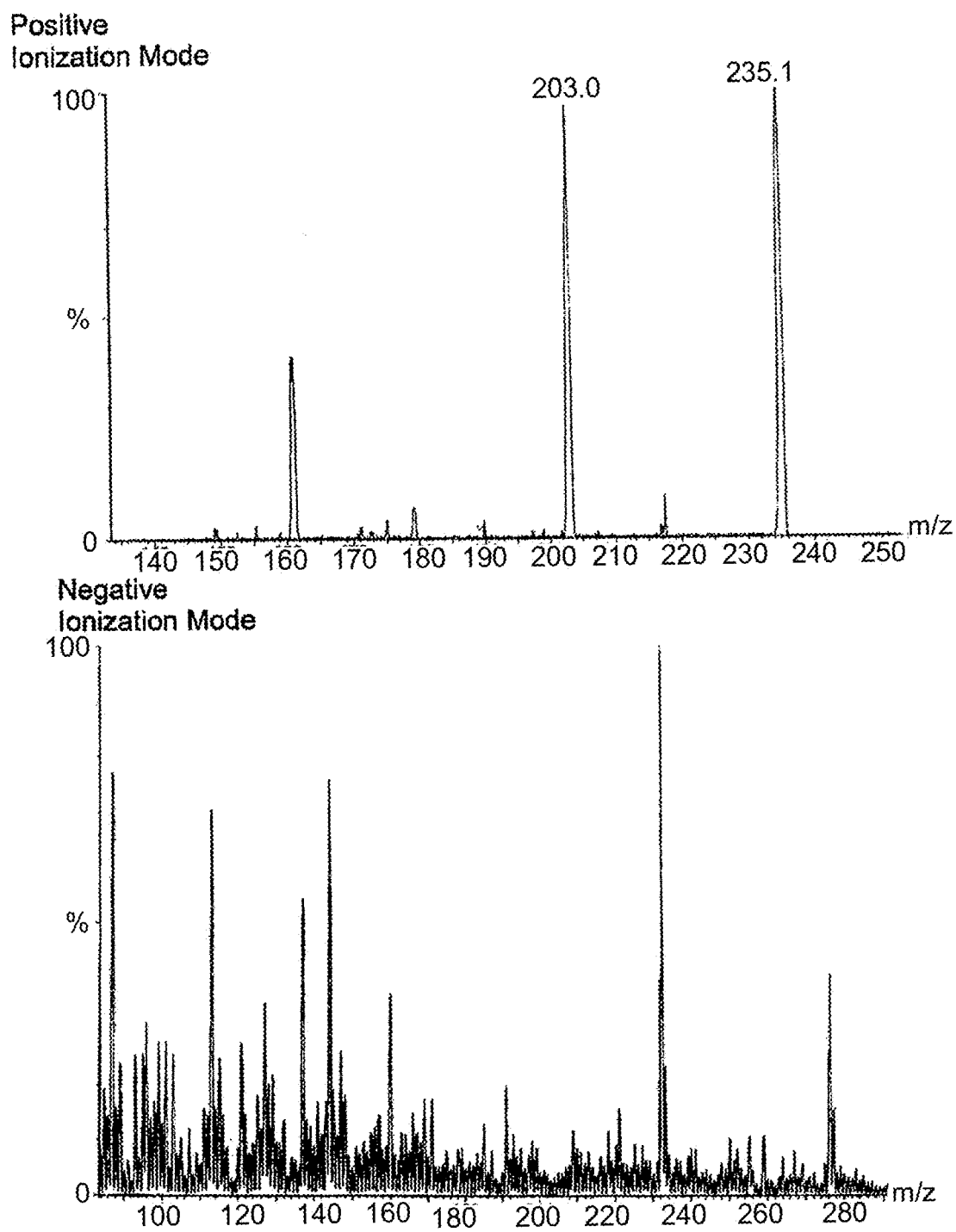
FIG. 12a shows the APCI-MS analysis of a saturated HgO(aq) solution at pH 7 (~1 nmol HgO) where HgO/Hg $(OH)_2$ detected by positive ionization APCI-MS.
Figure 13:
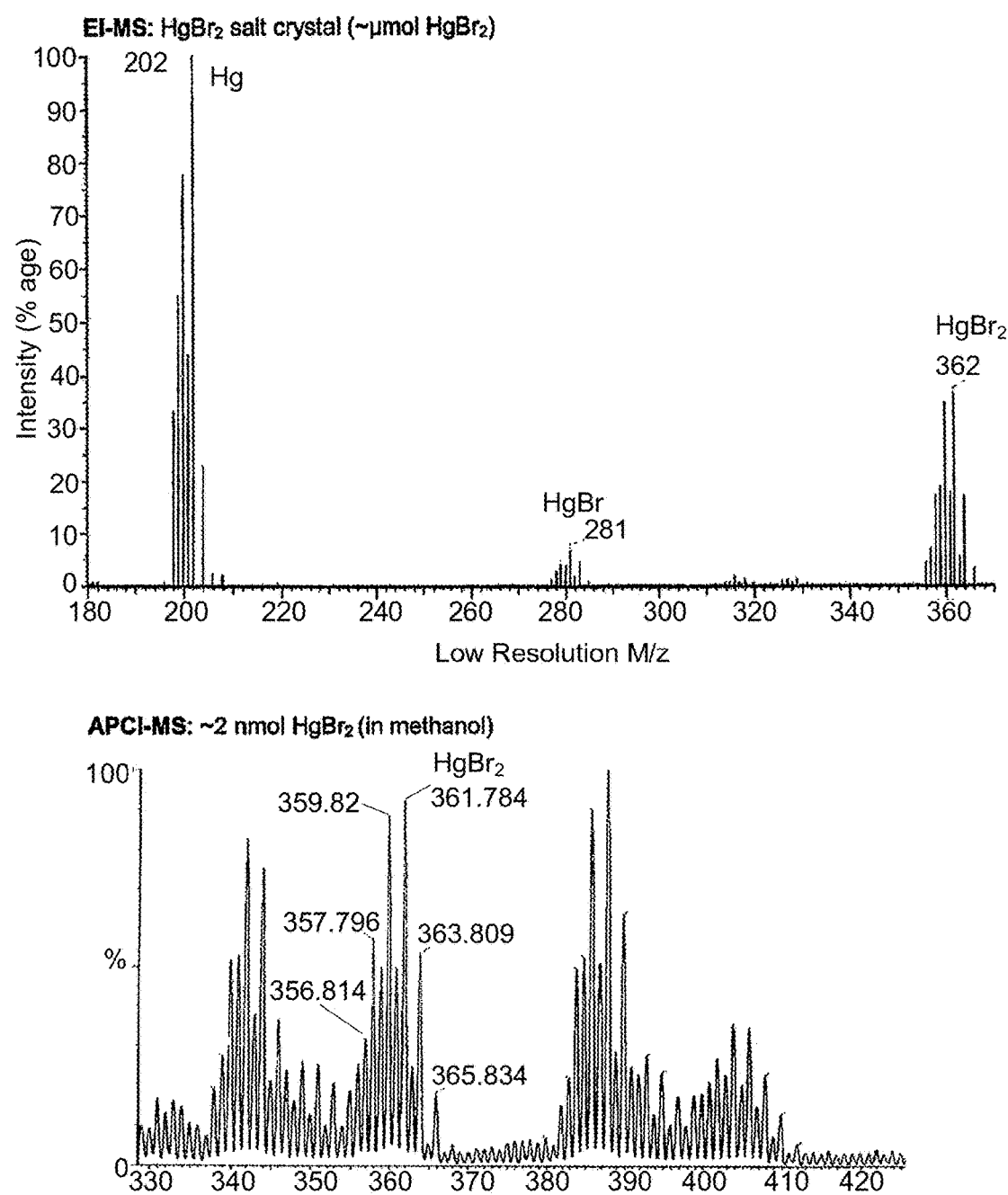
FIG. 13 shows the comparison of EI-MS and APCI-MS for retention of the molecular ion HgBr2.

The sensitivity of mass spectrometry for various mercury containing compounds is not identical. FIGS. 12a and 12b are a few examples showing, for instance, that mercury halide species such as $HgCl_2$ are best detected using the negative ionization mode, whereas compounds such as $HgO/Hg(OH)_2$ are detected better using the positive ionization mode.

f. Advantages of Soft-Ionization for Mercury Quantitative Analysis in Comparison to More Energetic (Harsh) Ionization We performed a series of experiments in the laboratory to evaluate which mass spectrometry instruments could provide more sensitive signals for mercury containing species. As shown in FIG. 13, soft-ionization techniques (such as APCI-MS) are shown to be more sensitive and retain more of the molecular ions of $HgBr_2$ than stronger ionization source, such as electron impact mass spectrometer (EI-MS).

g. Ambient Air and Water Matrices Measurements: Comparison with Total RGM Data

Results indicating that:

A wide range of mercury species quantified and identified in air and water

The technique is recyclable and a single trap/fiber can be used several times and be recovered upon thermal desorption.

Figure 14A:
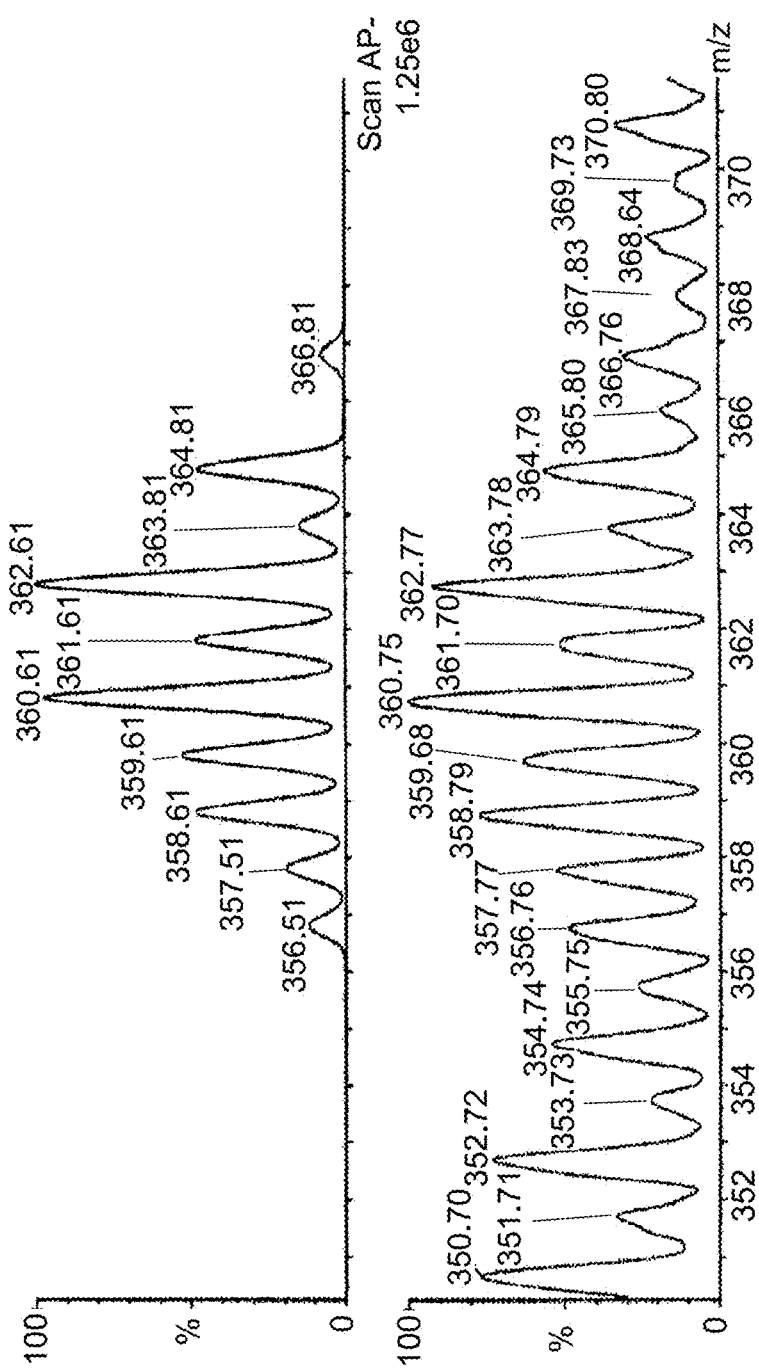
FIG. 14a, b, and c show some examples of real mercury speciation in range of detection of <20 ppt: a) $HgBr_2$, b) Oxygenated mercury compounds $(HgO/Hg(OH)_2)$ complexes in aquatic media, c) Blank samples for pure air; several blanks including $N_2$ and He were used.
Figure 14B:
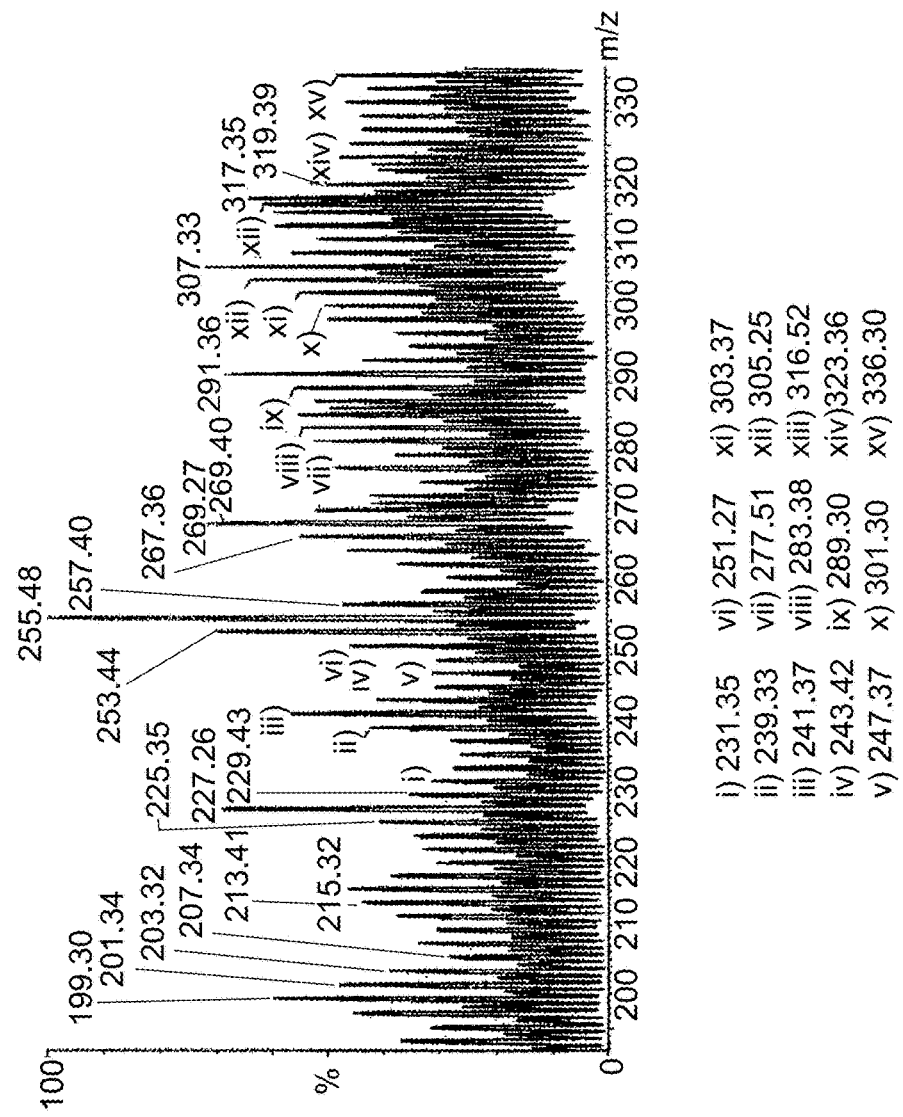
Figure 14C:
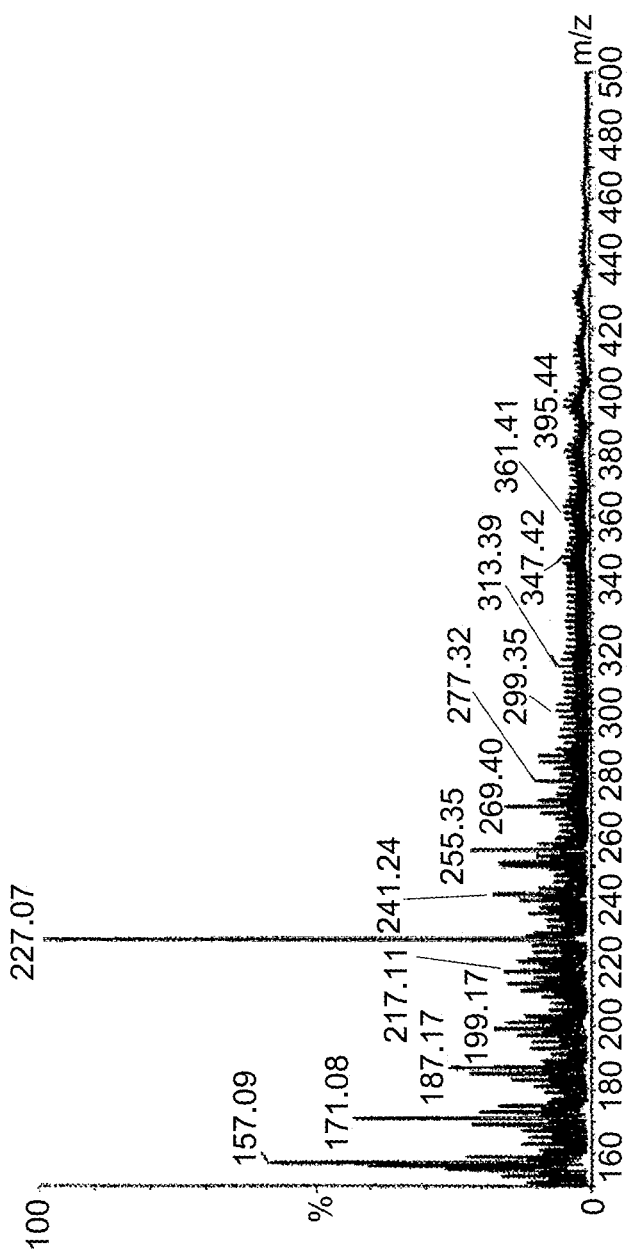

Time resolution average for most atmospheric measurement experiments are up to now currently 24 hours. We have performed experiments from 3 hours to 3 days. The 24-hour averages are comparable or better than all existing techniques that do not yield real chemical speciation. Quantification limits: Some examples of real mercury speciation in range of <20 ppt levels. Some examples for selected chemical speciation species in air are in FIGS. 14a to c.

It is to be noted that there is a large natural variation (temporal and spatial) for mercury containing compounds, as it is the case for most atmospheric chemical components. Based on our determination of concentrations, the concentrations when filters were not used, led to about 80 ppt levels, which indicates that some reactive mercury might be associated to particles.

It should be appreciated that the invention is not limited to the particular embodiments described and illustrated herein but includes all modifications and variations falling within the scope of the invention as defined in the appended claims. For example, the present invention can be applied to other metals other than mercury. These other metals may also have different species and therefore also may be identified and quantified using the present invention.

REFERENCES

Every document, reference, patent, patent application publication, referred to below and/or throughout the application is hereby incorporated by reference in its entirety for all purposes.

1. Mercury fate and transport in the global atmosphere, Pirrone and Mason, editors, Springer, pp, 459-501, ISBN: 987-0-387-93957-5 (2009).
2. P. A. Ariya, A. F. Khalizov, and A. Gidas, "Reaction of Gaseous Mercury with Atomic and Molecular Halogens: Kinetics, Product Studies, and Atmospheric Implications", Journal of Physical Chemistry A, 106(32), 7310-7320, (2002).
3. S. Coquet and P. Ariya, "The temperature dependence of Cl-atom initiated reactions of selected alkenes under tropospheric conditions", International Journal of Chemical Kinetics, 32, 478-488, (2000).

The invention claimed is:

1. A system for identifying and quantifying metal species, the system comprising:
   a) a collection interface unit for collecting a sample and concentrating an analyte, wherein the collection interface unit comprises a plurality of different interfaces, each interface including a surface onto which one analyte from one sample is collected, wherein the plurality of interfaces are configured to collect both gas-phase analytes and particulate-phase analytes;
   b) a soft ionization mass spectrometer which is configured to identify and quantify a content of each analyte in terms of metal species contained therein; and
   c) a flow tube for connecting an outlet of the collection interface unit to an inlet of the soft ionization mass spectrometer;
   wherein each interface defines a distinct sample flow path to the inlet of the soft ionization mass spectrometer;
   a plurality of flow control units associated with the sample flow paths and controllable such that only one sample is analyzed by the soft ionization mass spectrometer.

2. The system of claim 1, wherein the system is configured to identify and quantify metal species that are based on mercury, and comprise at least one species selected from HgBr2, HgCl2, HgI2, HgCl, HgBr, HgI, HgO, Hg(OH)2, and CH3HgCl.

3. The system of claim 1, wherein the sample includes air, liquid, water, ice, or snow.

4. The system of claim 1, wherein the plurality of collection interfaces comprises two or more of: (a) single layer or multi-layers of one of macro-particles, micro-particles, or nano-particles, or a combination thereof; (b) beads or wire coated with one of macro-particles, micro-particles, or nano-particles, or a combination thereof; (c) a tube coated with macro/micro/nano-particles; (d) a tube containing one of macro-particles, micro-particles, or nano-particles beads or wire, or a combination thereof; (e) uncoated beads; (f) uncoated wire; and (g) uncoated tube.

5. The system of claim 4, wherein the one of macro-particles, micro-particles, or nano-particles comprise gold- or sulfur-containing compounds, or a combination thereof; and wherein the beads are glass or metal.

6. The system of claim 1, wherein the plurality of collection interfaces are adapted for connection in parallel or in series.

7. The system of claim 1, wherein the collection interface unit comprises a first and a second collection interface, the first collection interface including gold- or sulfur-containing one of macro-particles, micro-particles, or nano-particles or a mixture of gold- and sulfur- containing one of macro-particles, micro-particles, or nano-particles, and the second collection interface including uncoated glass beads.

8. The system of claim 1, further comprising at least one aerosol sizer or at least one filter for removing particulates from the sample before the sample is collected.

9. A system for identifying and quantifying mercury species in both a gas phase and a condensed phase, the system comprising:
   a) a collection interface unit for collecting a sample and concentrating an analyte;
   b) a soft ionization mass spectrometer; and
   c) a flow tube for connecting an outlet of the collection interface unit to an inlet of the soft ionization mass spectrometer;
   wherein the collection interface unit comprises at least particles disposed within the flow tube and is configured for analyte capture/adsorption;
   wherein there is a plurality of collection interface units, each collection interface unit defining a distinct, independent sample flow path to the inlet of the soft ionization mass spectrometer, each sample flow path having an independent control valve for controlling sample flow to the soft ionization mass spectrometer such that only one sample is analyzed at one time within the soft ionization mass spectrometer;
   wherein the plurality of collection interface units is configured to act as a series of physical and physicochemical traps for the collection of measurable quantities of oxidized mercury from volumes of air samples, the traps including at least one of glass tubing containing gold coated glass beads, uncoated quartz beads, gold wire, and polysulfide-silanized glass beads.

10. The system of claim 9, wherein each trap includes nichrome wire wrapped therearound to provide a heating source for desorption of analytes into the soft ionization mass spectrometer.

* * * * *